United States Patent [19]

Neef et al.

[11] Patent Number: 5,532,228

[45] Date of Patent: Jul. 2, 1996

[54] SIDE-CHAIN HOMOLOGOUS VITAMIN D DERIVATIVES, PROCESS FOR THEIR PRODUCTION, PHARMACEUTICAL PREPARATIONS CONTAINING THESE DERIVATIVES AND THEIR USE AS PHARMACEUTICAL AGENTS

[75] Inventors: Gunter Neef; Gerald Kirsch; Andreas Stein-Eyer; Katica Schwarz; Matthias Bräutigam; Ruth Thieroff-Ekerdt; Petra Rach, all of Berlin, Germany

[73] Assignee: Schering Aktiengesellschaft, Berlin, Germany

[21] Appl. No.: 69,805

[22] Filed: Jun. 1, 1993

Related U.S. Application Data

[63] Continuation of Ser. No. 777,519, Dec. 6, 1991, abandoned.

[30] Foreign Application Priority Data

Feb. 6, 1990 [DE] Germany .................. 40 03 854.8
Oct. 30, 1990 [DE] Germany .................. 40 34 730.3

[51] Int. Cl.$^6$ .................. A61K 31/59; C07C 401/00
[52] U.S. Cl. .................. 514/167; 552/653; 540/200; 540/202; 544/2; 544/3; 544/63; 544/224; 546/1; 548/100; 548/122; 548/123; 548/124; 548/125; 548/400; 549/1; 549/13; 549/29; 549/88
[58] Field of Search .................. 514/167; 552/653; 540/200, 202; 544/2, 3, 63, 224; 546/1; 548/100, 122, 123, 124, 125, 400; 549/1, 13, 29, 88, 90, 200, 356, 429, 549, 510, 512

[56] References Cited

U.S. PATENT DOCUMENTS 4,267,117  5/1981  Salmond .................. 260/397.2

FOREIGN PATENT DOCUMENTS 441467  8/1991  European Pat. Off. ...... C07C 401/00
2526981  1/1976  Germany .................. A61K 31/59
3541933  6/1986  Germany .................. C07C 175/00
658050  10/1986  Switzerland .................. C07C 172/00
02562  11/1980  WIPO .................. C07J 9/00

Primary Examiner—Kimberly J. Prior
Attorney, Agent, or Firm—Millen, White, Zelano & Branigan

[57] ABSTRACT

The invention discloses side-chain homologous vitamin D derivatives of formula I

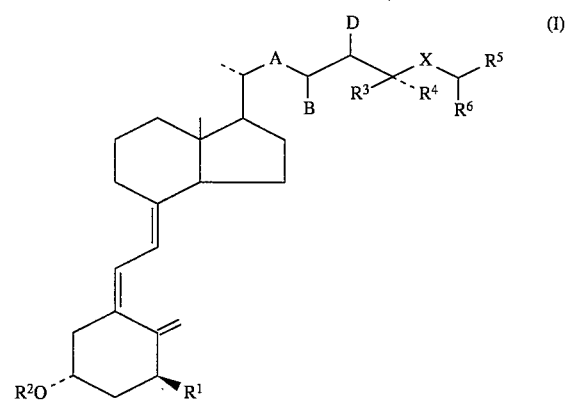

in which $R^1, R^2, R^3, R^4, R^5, R^6$, B, and D have the meanings defined in the specification and either (1) A is a direct bond between carbon atoms 20 and 22 and X is an oxy alkylene radical, —$(CH_2)_nO$— where n is 1 to 3; (2) A is a methylene bridge, —$CH_2$—, between carbon atoms 20 and 22 and X is either an alkylene radical, —$(CH_2)_n$— or an oxy alkylene radical, —$(CH_2)_nO$—, where n is 1 to 3; or (3) if A is a direct bond and B and D together form a second bond, then $X(R^5)(R^6)$ is

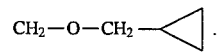

The compounds possess proliferation-inhibiting and cell-differentiating activity.

10 Claims, No Drawings

SIDE-CHAIN HOMOLOGOUS VITAMIN D DERIVATIVES, PROCESS FOR THEIR PRODUCTION, PHARMACEUTICAL PREPARATIONS CONTAINING THESE DERIVATIVES AND THEIR USE AS PHARMACEUTICAL AGENTS

This is a continuation of application Ser. No. 07/777,519 filed Dec. 6, 1991 now abandoned.

This invention relates to side-chain homologous vitamin D derivatives of formula I

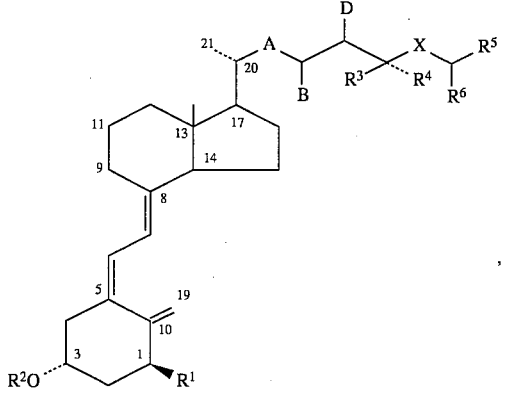

in which

R$^1$ means a hydrogen atom, a hydroxy or an acyloxy group with 1 to 9 carbon atoms, R$^2$ means a hydrogen atom or an acyl group with 1to 9 carbon atoms, R$^3$ or R$^4$ means a hydroxy or acyloxy group with 1 to 9 carbon atoms, and the respective other substituent is a hydrogen atom or R$^3$ and R$^4$ together mean an oxygen atom, R$^5$ and R$^6$, independently of one another, each mean a linear or branched alkyl radical with up to 5 carbon atoms, a trifluoromethyl group or together a saturated, unsaturated or aromatic carbocyclic 3-, 4-, 5- or 6-member ring formed with the tertiary carbon atom or with the inclusion of 1 or 2 N, O or S atoms a heterocyclic 3, 4, 5 or 6-member ring, B and D either mean a hydrogen atom each or together a second bond (E-configured double bond) and either A means a direct bond between carbon atoms 20 and 22 and X means an oxy alkylene radical —(CH$_2$)$_n$O— with n=1 to 3 or A means a methylene bridge (—CH$_2$—) between carbon atoms 20 and 22 and X means an alkylene radical —(CH$_2$)$_n$— or an oxy alkylene radical —(CH$_2$)$_n$O— with n=1 to 3, or if A stands for a direct bond and B and D together stand for a second bond

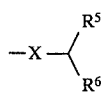

means one of radicals

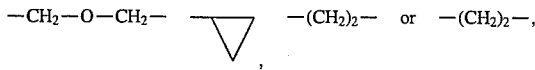

as well as a process for their production, pharmaceutical preparations that contain these compounds and their use for the production of pharmaceutical agents.

The acyloxy or acyl groups possible for radicals R$^1$, R$^2$ and within radicals R$^3$ or R$^4$ are derived in particular from saturated carboxylic acids or also from benzoic acid. Other suitable acyl radicals in R$^1$, R$^2$, R$^3$, R$^4$ comprise those which are cyclic, acyclic, carboxylic or heterocyclic—all optionally also unsaturated. The preferred radicals are derived from C$_1$- to C$_9$-, preferably C$_2$- to C$_5$-, alkanecarboxylic acids, such as, for example, acetyl, propionyl, butyryl.

If R$^5$ and R$^6$ form, together with the tertiary carbon atom, a saturated carboxylic ring, then the cyclopropyl or cyclohexyl ring is especially referred to. As alkyl groups for R$^5$ and R$^6$, those with 1 to 5 carbon atoms, which can be straight-chain or branched, are especially suitable. By way of example, there can be mentioned the methyl, ethyl, propyl and t-butyl group.

Preferred according to this invention are side-chain homologous vitamin D derivatives of general formula I, in which R$^1$, R$^3$ or R$^4$ stands for a hydroxy group or R$^5$ and R$^6$ stand for a methyl group or, together with the tertiary carbon atom, for a cyclopropyl ring, R$^2$ stands for a hydrogen atom and n is 1 or 2.

Between carbons atoms 22 and 23 (when A means a direct bond) or between carbon atoms 23 and 24 (when A means a methylene group), there is preferably a double bond. Especially preferred are the compounds 24-(1(R)-Hydroxy-4-methylpentyl)-9,10-secochola-5Z,7E,10(19),23E-tetraene-1(S),3(R)-diol, 24-(1(S)-hydroxy-4-methylpentyl)-9,10-secochola-5Z,7E,10(19),23E-tetraene-1(S),3(R)-diol, 24-(1(R)-hydroxy-3-methylbutyl)-9,10-secochola-5 Z,7E,10(19),23E-tetraene-1(S),3(R)-diol, 24-(1(S)-hydroxy-3-methylbutyl)-9,10-secochola-5Z,7E,10(19),23E-tetraene-1(S),3(R)-diol, 24-(1(R)-hydroxy-3-methylbutyl)-9,10-secochola-5Z,7E,10(19)-triene-1(S),3(R)-diol, 24-(1(S)-hydroxy-3-methylbutyl)-9,10-secochola-5Z,7E,10(19)-triene-1(S),3(R)-diol, 24-(1(R)-hydroxy-3-isopropoxypropyl)-9,10-secochola-5Z,7E,10(19),23E-tetraene-1(S),3(R)-diol, 24-(1(S)-hydroxy-3-isopropoxypropyl)-9,10-secochola-5Z,7E,10(19),23E-tetraene-1(S),3(R)-diol, 24-isopropoxymethyl-9,10-secochola-5Z,7E,10(19),22E-tetraene-1(S),3(R),24(R)-triol, 24-isopropoxymethyl-9,10-secochola-5Z,7E,10(19),22E-tetraene-1(S),3(R),24(S)-triol, 24-(2-isopropoxyethyl)-9,10-secochola-5Z,7E,10(19),22E-tetraene-1(S),3(R),24(R)-triol, 24-(2-isopropoxyethyl)-9,10-secochola-5Z,7E,10(19),22E-tetraene-1(S),3(R),24(S)-triol, 26,27-cyclo-24a,24b-dihomo-9,10-secocholesta-5Z,7E,10(19),23E-tetraene-1(S),3(R),24a(R)-triol, 26,27-cyclo-24a,24b-dihomo-9,10-secocholesta-5Z,7E,10(19),23E-tetraene-1(S),3(R),24a(S)-triol.

Natural vitamins D$_2$ and D$_3$ (cf. general formula V) are biologically inactive in and of themselves and are converted only after hydroxylation in 25-position in the liver or in 1-position in the kidneys into their biologically active metabolites. The effect of vitamins D$_2$ and D$_3$ consists in stabilizing the plasma Ca$^{++}$ level and the plasma phosphate level; they counteract a decrease in the plasma Ca++ level.

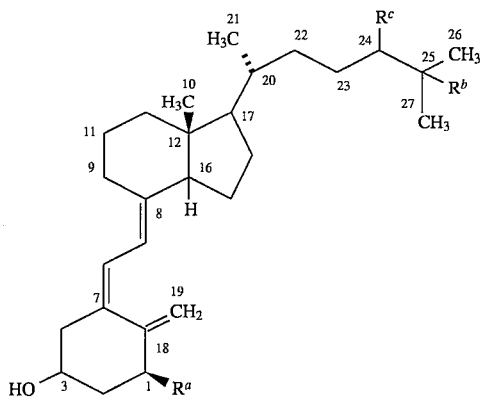

ergocalciferol: $R^a = R^b = H$, $R^c = CH_3$, vitamin $D_2$ double bond c-22/23 cholecalciferol: $R^a = R^b = R^c = H$ vitamin $D_3$ 25-hydroxycholecalciferol: $R^a = R^c = H$, $R^b = OH$ 1alpha-hydroxycholecalciferol: $R^a = OH$, $R^b = R^c = H$ 1alpha, 25-dihydroxycholecalciferol: $R^a = R^b = OH$, $R^c = H$ calcitriol Besides their pronounced effect on the calcium and phosphate metabolism, vitamins $D_2$ and $D_3$ and their synthetic derivatives also have proliferation-inhibiting and cell-differentiating effects (H. F. De Luca, The Metabolism and Function of Vitamin D in Biochemistry of Steroid Hormones, publisher H. L. J. Makin, 2nd Edition, Blackwell Scientific Publications 1984, pages 71–116).

But overdose phenomena can occur when using vitamin D (hypercalcemia).

lalpha-Cholecalciferols hydroxylated in 24-position already follow from DE-AS-25 26 981; they have a lower toxicity than the corresponding nonhydroxylated lalpha-cholecalciferol. The hydroxylated compounds show a selective activation of the intestinal calcium absorption and a weaker bone absorption effect than lalpha-cholecalciferol. The 24-hydroxy vitamin D analogs described in international patent application WO 87/00834 can be used for treating disorders caused by abnormal cell proliferation and/or cell differentiation in humans and animals.

For various 1,25-dihydroxy-homo vitamin D derivatives, a dissociation with respect to the properties of the bone absorption effect and HL 60 cell differentiation has already been briefly mentioned by De Luca. The in vitro bone absorption effect here is a direct measurement for the in vivo calcium mobilization.

It has now been found that the side-chain homologous vitamin D derivatives of general formula I according to the invention surprisingly exhibit a more favorable spectrum of action compared with the vitamin D derivative calcitriol (lalpha,25-dihydroxycholecalciferol). While the effects on the calcium and phosphate metabolism are clearly weakened (decrease of the side effects from overdosing or necessary higher dosage), the proliferation-inhibiting and cell-differentiating effects are approximately maintained (dissociation).

The vitamin D activity of the compounds according to the invention is determined by the calcitriol receptor test. It is performed by using a specific receptor protein from the intestine of rachitic chickens.

A binding protein containing a receptor is incubated with $^3$H-calcitriol (0.5 ng/ml) in a reaction volume of 0.575 ml in the absence and in the presence of the test substances for one hour in a test tube. To separate the free calcitriol from the calcitriol bound to the receptor, a charcoal-dextran absorption is performed. For this purpose, 200 microliters of a charcoal-dextran suspension is fed to each test tube and incubated for 30 minutes at 22° C. Then, the samples are centrifuged at 1,500×g for 10 minutes at 4° C. The supernatant fluid is decanted and measured in a beta-counter after about 1 hour of equilibration in atom light.

The competition curves obtained with various concentrations of the test substance and of the reference substance (unlabeled calcitriol) with a constant concentration of the standard substance ($^3$H-calcitriol) are placed in relation to one another and a competition factor (KF) is determined.

It is defined as the quotient of the concentrations of the respective test substance and of the reference substance that are necessary for 50% competition:

$$KF = \frac{\text{concentration of the test substance at 50\% competition}}{\text{concentration of the reference substance at 50\% competition}}$$

According to this, 24-(1-hydroxy-3-methylbutyl)-9,10-secochola-5Z,7E,10(19),23E-tetraene-1(S),3(R)-diol (compound A) has a KF value of 2.0 and 24-(1-hydroxy-3-methylbutyl)-9,10-secochola-5Z,7E,10(19),23E-tetraene-1(S),3(S)-diol (compound B) has a KF-value of 3.6.

To determine the antiproliferative power of the compounds according to the invention, the test described below is performed instead with compounds A and B as test substances:

Keratinocytes of newborn mice are prepared and cultivated in a modification of the method of Yuspa, S. and Harris, C. C., "Altered differentiation of mouse epidermal cells treated with retinyl acetate in vitro," Exp Cell Res 86: 95–105, 1974.

Neonatal NMRI mice of both sexes are killed by decapitation, the skin is removed, washed in an antibiotic-antimycotic solution and, with the dermal side facing down, incubated overnight at 4° C. in dispase II solution (1.2 U/ml in tissue culture medium M199 +25 mmol/l HEPES+15% fetal calf serum (FCS)+50 U/ml of penicillin/streptomycin (P/S) (preparation medium, PM). The epidermis is removed and a single-cell suspension is produced by trypsinization. After centrifuging, the cell sediment is resuspended, the number of living, small, round cells is determined after trypan blue staining and the cells are sown in a density of $4 \times 10^5$ cells/cm$^2$ in Primaria 24-hole plates in tissue culture medium (M199+15% FCS+50 U/ml of P/S). After 24 hours of incubation at 37° C., the cells are washed with phosphate-buffered saline solution (PBS) and incubated for another 24 hours in serum-free tissue culture medium (M199+50 U/ml of P/S+0.5% ethanol) with and without test substances at 32.5° C. Then, 0.4 microcuries/50 microliters of $^3$H-methylthymidine (40 Ci/mmol) is added. After 4 hours, the medium is suctioned off and the reaction is ended by adding 500 microliters of ice-cold 10% trichloroacetic acid (TCA). The cells are washed with TCA and PBS, lysed by incubation in a proteinase K-solution (10 mmol/l of tris-HCl, 10 mmol/l of EDTA, 10 mmol/l of NaCl, 0.2% triton-X 100, pH 8.0, 50 micrograms/ml of protein kinase K) and the lysate is clarified by centrifuging. In the supernatant fluid, the radioactivity is determined by scintillation photometry and, after specific staining of the DNA with diamidinophenylindole (DAPI), the DNA concentration is determined by fluorescence photometry.

Accordingly depending on the dose, calcitriol and compounds A and B inhibit the $^3$H-thymidine incorporation in DNA with the following $IC_{50}$ values:

| | |
|---|---|
| calcitriol | $2 \times 10^{-9}$ mol/l |
| compound A | $1 \times 10^{-8}$ mol/l |
| compound B | $3.2 \times 10^{-9}$ mol/l |

The effects of calcitriol and of the compounds according to the invention that stimulate the differentiation 26,27-cyclo-24a,24b-dihomo-9,10-secocholesta-5Z,7E, 10(19),23E-tetraene-1(S),3(R),24a(R)-triol (compound C) and 26,27-cyclo-24a,24b-dihomo-9,10-secocholesta-5Z,7E, 10(19),23E-tetraene-1(S),3(R),24a(S)-triol (compound D) practically do not differ.

It is known from the literature (Mangelsdorf, D. J. et al, J. Cell. Biol. 98: 391–398 (1984)) that the in vitro treatment of human leukemia cells (promyelocytic cell line HL 60) with calcitriol induces the differentiation of the cells into macrophages.

To quantify the differentiation-stimulating effect of calcitriol analogs, the test indicated below was performed:

HL 60 cells are cultivated in tissue culture medium (RPM1—10% fetal calf serum) at 37° C. in an atmosphere of 5% $CO_2$ in air.

To test the substance, the cells are separated by centrifuging and $2.8\times10^5$ cells/ml are taken up in phenol red-free tissue culture medium. The test substances are dissolved in ethanol and diluted with tissue culture medium without phenol red to the desired concentration. The dilution stages are mixed with the cell suspension in a ratio of 1:10 and 100 microliters each of this cell suspension mixed with substance is pipetted into an indentation of a 96-hole plate. As a control, a cell suspension is mixed analogously with the solvent.

After incubation for 96 hours at 37° C. in 5% $CO_2$ in air, 100 microliters of an NBT-TPA solution (nitro blue tetrazolium (NBT), final concentration in the batch 1 mg/ml, tetradecanoyl-phorbol myristate-13-acetate (TPA), final concentration in the batch $2\times10^{-7}$ mol/l) is pipetted into each indentation of the 96-hole plate into the cell suspension.

By incubation for 2 hours at 37° C. and 5% $CO_2$ in air, the NBT is reduced to insoluble formazan because of the intracellular oxygen radical release, stimulated by TPA, in the cells differentiated into macrophages.

To end the reaction, the indentations of the 96-hole plate are drained and the adhering cells are fixed by adding methanol and dried after fixation.

To dissolve the intracellular formazan crystals formed, 100 microliters of potassium hydroxide (2 val/l) and 100 microliters of dimethyl sulfoxide are pipetted into each indentation and are exposed to ultrasonic waves for 1 minute. The concentration of formazan is measured by spectrophotometry at 650 nm.

The concentration of formazan formed is regarded as a measurement for the differentiation induction of the HL 60 cells into macrophages. The relative effectiveness of the test substance results from the quotient of $ED_{50}$ test substance/$ED_{50}$ calcitriol.

According to this, calcitriol, compound C and compound D have the $ED_{50}$ values $1.8\times10^{-9}$ mol/l, $2.2\times10^{-9}$ mol/l or $2.5\times10^{-9}$ mol/l.

Because of the reduced risk of hypercalcemia, the substances according to the invention are especially suited for the production of pharmaceutical agents for treating diseases which are characterized by a hyperproliferation, e.g., hyperproliferative diseases of the skin (psoriasis) and malignant tumors (leukemia, colon cancer, breast cancer). In an especially preferred embodiment of the invention, calcitriol receptors are detected in the target organ before the treatment.

This invention thus also relates to pharmaceutical preparations that contain at least one compound according to general formula I together with a pharmaceutically compatible vehicle. The compounds can be formulated as solutions in pharmaceutically compatible solvents or as emulsions, suspensions or dispersions in suitable pharmaceutical solvents or vehicles or as pills, tablets or capsules that contain solid vehicles in the way known in the art. For a topical use, the compounds are advantageously formulated as creams or ointments or in a similar pharmaceutical agent form suitable for topical use. Each such formulation can also contain other pharmaceutically compatible and nontoxic auxiliary agents such as, e.g., stabilizers, antioxidants, binders, dyes, emulsifiers or flavoring substances. The compounds are advantageously administered by injection or intravenous infusion of suitable sterile solutions or as oral dosage through the alimentary tract or topically in the form of creams, ointments, lotions or suitable transdermal plasters, as described in EP-A-0387 077.

The daily dose is 0.1 microgram/patient/day—1,000 micrograms (1 mg)/patient/day, preferably 1.0 microgram/patient/day—500 micrograms/patient/day.

The compounds according to the invention are generally administered analogously to the administration of the known agent "calcipotriol" for the treatment of psoriasis.

Further, the invention relates to the use of the compounds according to formula I for the production of pharmaceutical agents.

The production of side-chain homologous vitamin D derivatives of formula I is performed according to the invention in that a compound of general formula IV

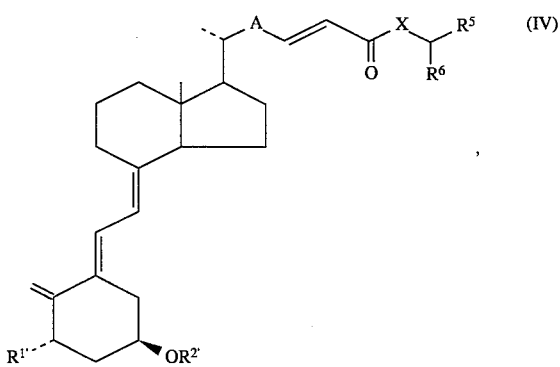

in which

R$^{1'}$ means a hydrogen atom or a protected hydroxy group and

R$^{2'}$ means a hydroxy protecting group and

A, X and R$^5$ and R$^6$ have the meaning given in formula I, optionally after selective hydrogenation of the double bond in the side chain, is converted into a compound of general formula IVa

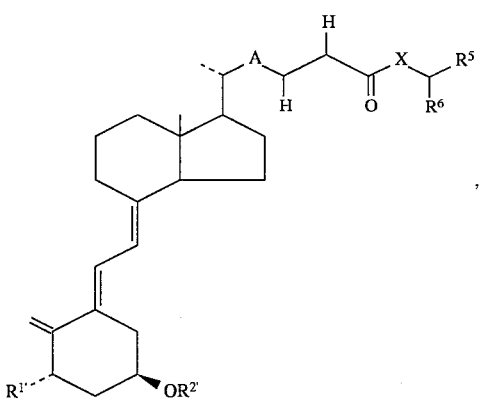

in which $R^{1'}$, $R^{2'}$, A, X and $R^5$ and $R^6$ have the meaning given in formula IV and optionally, after reduction of the carbonyl function and optionally after separation of the mixture of the epimeric hydroxy compounds of general formulas IIIA and IIIB formed by the reduction

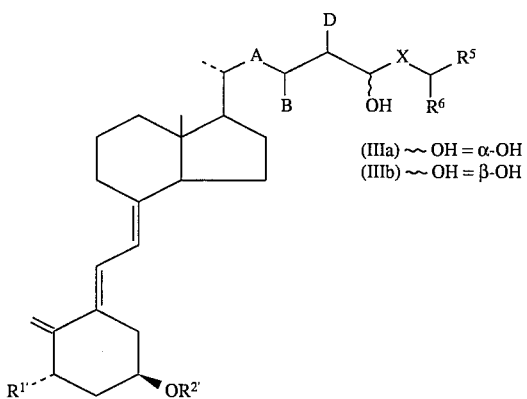

(IIIa) ∼ OH = α-OH
(IIIb) ∼ OH = β-OH in which $R^1$, $R^2$, A, X and $R^5$ and $R^6$ have the meaning given in formula IV and B and D have the meaning given in formula I, by irradiation with ultraviolet light with reversal of the stereoisomerism at the 5,6 double bond, is converted into a compound of general formula II

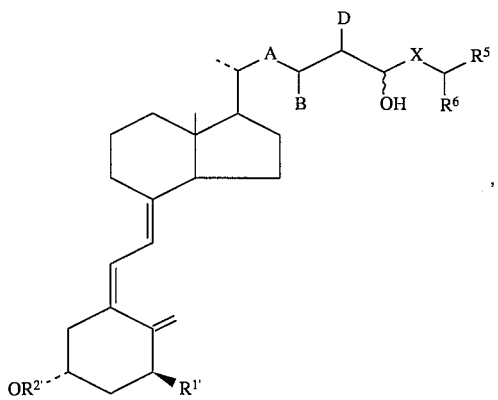

in which $R^{1'}$, $R^{2'}$, A, B, D, X and $R^5$ and $R^6$ have the meaning given in formula IIIa/IIIb, and then the latter, by the cleaving of existing hydroxy protecting groups and optionally by partial or complete esterification of the hydroxy groups, is converted into a compound of general formula I.

The reduction of the side-chain carbonyl function in the compound of general formula IV is performed for example with cerium(III) chloride/sodium borohydride in a polar solvent. Both the R and the S hydroxy isomer of general formula IIIa or IIIB result during the reduction. Both isomers can be separated chromatographically.

Optionally, before reduction of the carbonyl function, the double bond in the side chain can be selectively hydrogenated. As hydrogenation agent, lithium-tri-tert-butoxy-aluminum hydride in a polar solvent is suitable, among others.

The following conversion of a compound of general-formula. IIIa/IIIb into a compound of general formula II is performed, e.g., by irradiation with ultraviolet light in the presence of a so-called "triplet sensitizer." In the framework of this invention, anthracene is used for this purpose. By cleaving the pi-bond of the 5,6 double bond, rotating the A ring by 180° around the 5,6 single bond and reestablishing the 5,6 double bond, the stereoisomerism at the 5,6 double bond is reversed.

Then, available hydroxy protecting groups are cleaved, preferably by using tetra-n-butyl-ammonium fluoride and optionally the free hydroxy groups are esterified according to current processes partially or completely with the corresponding carboxylic acid halide (halide=chloride, bromide) or carboxylic acid anhydride.

Production of the initial materials 1. 1(S),3(R)-bis—(tert-Butyldimethylsilyloxy)-20(S)-formyl-9,10- secopregna-5E,7E,10(19)-triene 1:

The production of 1 is performed according to M. J. Calverley, Tetrahydron 43, 4609 (1987); see also international patent application WO 87/00834. The production of the initial compound in which $R^{1'}$ is a hydrogen atom is also described there.

2. 1(S),3(R)-bis-(tert-Butyldimethylsilyloxy)-20(R)-methyl-9,10-secopregna-5E,7E,10(19)-triene-21-carbaldehyde 2

Aldehyde 2 is produced according to a new process.

a. A solution of 15.57 g of diethyl phosphonoethoxy ethyl acetate (produced according to W. Grell and H. Machleidt, Liebigs Ann. Chem. 699, 53 (1966) in 200 ml of THF is instilled at 25° C. in a suspension of 1.8 g of sodium hydride (80% in oil) in 70 ml of abs. THF. After adding, it is stirred another 90 minutes at 60° C., cooled again to 25° C. and a solution of 6.2 g of 1 in 70 ml of THF is added drop by drop. It is stirred for 2 hours under reflux, the cooled reaction solution is then poured into water and extracted with ethyl acetate. After drying (Na$_2$SO$_4$) and concentration by evaporation, the crude product obtained is chromatographed on silica gel with hexane/ethyl acetate. The main fraction yields 5.2 g of 1(S),3(R)-bis—(tert-butyldimethylsilyloxy)- 23-(ethoxy-9,10-secochola-5E,7E,10(19)-tetraene-24-acid ethyl ester as an oily mixture of the C-22 double bond isomers.

b. 5.2 g of the product obtained under a. is dissolved in 120 ml of toluene and at 0° C. slowly mixed with 20 ml of a 20% solution of diisobutylaluminum hydride in toluene. After 30 minutes at 0° C., the reaction solution is poured carefully into NH$_4$Cl solution and extracted with ethyl acetate. After the usual working up, 4.88 g of 1(S),3(R)-bis-(tert-butyldimethylsilyloxy)-23 -ethoxy-9,10-secochola-5E,7E,10(19),22-tetraen-24-ol is obtained as a colorless, oily isomer mixture that is used in the next step without further purification.

c. The compound produced under b. (4.88 g) is stirred in a mixture of 55 ml of dichloromethane and 55 ml of a 70% aqueous acetic acid for 4 hours at room temperature. Then it is neutralized by adding NH₃ solution and extracted with dichloromethane. The crude product is chromatographed on silica gel with hexane/ethyl acetate. In this way, 2.02 g of 1(S),3(R)-bis-tert-butyldimethylsilyloxy)-24-hydroxy-9,10-secochola-5E, 7E,10,(19)-trien-23-one 5 is obtained as colorless oil.

¹H-NMR (CDCl₃): =0.01 ppm (s, 12H, Si—CH₃), 0.52 (s,3H, H-18), 0.81 and 0.84 (s; 9H, Si-t-butyl each), 0.90 (d, J =7 Hz, 3H, H-21), 3.09 (t, J=5 Hz, 1H, OH), 4.10 (dd, 1H, H-24), 4.16 (m, 1H, H-3), 4.21 (dd, 1H, H-24), 4.39 (m, 1H, H-1), 4.88, 4.93 (s; 1H, H-19 each), 5.77, 6.39 (d, J=11 Hz; 1H, H-6, H-7 each).

d. The product obtained under c. (2.02 g) is dissolved in 25 ml of methanol and 25 ml of THF and mixed at 0° C. with 300 mg of sodium borohydride. It is stirred for 1.5 hours at 0° C., the reaction mixture is then poured into NH₄Cl solution and extracted with ethyl acetate. 1.75 g of 1(S), 3(R)-bis-(tert-butyldimethylsilyloxy)-9,10-secochola-5E,7E,10,(19)-triene-23,24-diol 6 is obtained as a colorless, oily mixture of the 23-epimers that is used as such in the next reaction.

e. 1.75 g of the product obtained under d. is dissolved in 40 ml of toluene and 1.23 g of lead tetraacetate is added in portions with ice water cooling. It is stirred for 30 minutes, 1.0 g of Pb(OAc)₄ is again added and it is stirred for another 15 minutes at +5 to +10° C.

For the working up, it is mixed with NaHCO₃ solution, the resulting suspension is filtered over cellite and the filtrate is extracted with ethyl acetate. The crude product is chromatographed on silica gel with hexane/ethyl acetate. After crystallization of the main fraction from ethanol, 560 mg of 1(S),3(R)-bis-(tert-butyldimethylsilyloxy)-20(R)-methyl-9, 10- secopregna-5E,7E,10,(19)-triene-21-carbaldehyde with a melting point of 101–104° C. is obtained.

The reaction of aldehyde 1 or 2 with a phosphorane of formula

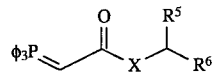

leads to the compounds of general formula IV (Wittig reaction).

Production of the phosphorus ylides used:

1. Isobutylcarbonylmethylenetriphenyl phosphorane a. Bromomethylisobutyl ketone 50 ml of isobutylmethyl ketone in 240 ml of methanol is mixed at 0° C. with 20 ml of bromine and, after being added, is stirred for another 1.5 hours at +10° C. After this, 360 ml of water is added and it is stirred for another 16 hours at room temperature.

For the working up, the reaction mixture is mixed with saturated common salt solution, the organic phase that precipitates is separated and the aqueous phase is extracted with ether. The combined organic phases are washed with 10% Na₂CO₃ solution and dried on Na₂SO₄. After filtration, the solvent is removed in the water jet vacuum and the residue is distilled. The main fraction contains 53.7 g of bromomethylisobutyl ketone of $b_p^{15-20}$ of 67°–69° C.

b. Isobutylcarbonylmethyltriphenylphosphonium bromide

Bromomethylisobutyl ketone (53.6 g) and triphenylphosphine (78.5 g) are intimately mixed in a 500 ml round-bottom flask and, after the initially strong heat tonality subsides, are left for 12 hours under nitrogen at room temperature. After that, the solid reaction mass is taken up in 330 ml of methylene chloride and refluxed for 30 minutes.

After adding 500 ml of ether, it is allowed to cool to room temperature and the product is isolated by filtration. After drying,111.7 g of the phosphonium salt with a melting point of 244–245° C. is obtained.

c. Isobutylcarbonylmethylenetriphenyl phosphorane 111.6 g of the phosphonium bromide obtained under b. is mixed successively with 1500 ml of methylene chloride and 1500 ml of 2N NaOH and stirred for 30 minutes at room temperature. The organic phase is separated, washed with water and dried on Na₂SO₄. The solid residue obtained after concentration by evaporation is recrystallized from tert-butyl methyl ether and yields 72.2 g of the ylide with a melting point of 120°–121° C.

2. Isoamylcarbonylmethylenetriphenyl phosphorane

The formation of the title compound is performed analogously to the process described under 1. by bromation of isoamylmethyl ketone, reaction of the bromide with triphenylphosphine to phosphonium salt and formation of the ylide with 2N NaOH.

After distillative purification,54.68 g of 1-bromo-5-methyl-hexan-2-one of $b_p^{15-20}$ of 80°–86° C. is obtained from 50.0 ml of isoamylmethyl ketone and 18.2 ml of bromine.

91.6 g of the phosphonium salt with a melting point of 230°–233° C. is obtained from 54.58 g of the bromide and 74.14 g of triphenylphosphine.

After treatment with NaOH and recrystallization of the crude product from methylene chloride/ester, 69.8 g of the title compound with a melting point of 64°–67° C. is obtained from 91.6 g of phosphonium salt.

3. Isopropoxymethylcarbonylmethylenetriphenyl phosphorane 2.43 g of sodium is dissolved in 150 ml of isopropanol. After adding 20.0 g of chloromethylcarbonylmethylenetriphenyl phosphonium ketone (R. F. Hudson et al., J. Org. Chem. 28 2446, 1963) dissolved in 200 ml of isopropanol, is refluxed for 8 hours.

The cooled reaction mixture is poured into a common salt solution and extracted with ethyl acetate. The oily residue obtained after concentration by evaporation is chromatographed on silica gel with ethyl acetate. 9.53 g of the title compound with a melting point of 134° C. is obtained.

4. (2-Isopropoxyethyl)-carbonylmethylenetriphenyl phosphorane a. 1-Bromo-4-isopropoxy-butan-2-one A solution of 68.2 g of 4-isopropoxy-2-butanone (F. B. Hasan et al., J. Biolog. Chem. 256, 7781, 1981) in 315 ml of methanol is mixed by instillation at 0° C. with 26.9 ml of bromine and then stirred for 1.5 hours at +10° C. Then 470 ml of water is instilled in the reaction solution and it is stirred for 16 hours at room temperature. For working up, it is poured into saturated common salt solution and extracted with ether. Distillation of the crude product yields 78.07 g of the bromine derivative of $b_p^{15-20}$ of 95° C.

b. 4-Isopropoxy-2-oxo-butyl-triphenylphosphonium bromide

According to the process described under 1, 133.35 g of phosphonium salt with a melting point of 183° C. is obtained from 78.0 g of the bromide obtained under a. and 97.85 g of triphenylphosphine.

c. (2-Isopropoxyethyl)-carbonylmethylenetriphenyl phosphorane

The phosphonium bromide (133.2 g) obtained under b. is treated as described under 1. with 2N NaOH in methylene chloride. After recrystallization of the crude product from ethyl acetate, 64.38 g of the title compound with a melting point of 97° C. is obtained. 5. (1-Ethylpropoxymethyl)-carbonylmethylenetriphenyl phosphorane A solution of 3.04 g of sodium in 100 ml of 3-pentanol is reacted with 25.0 g of chloromethylcarbonylmethylenetriphenyl phosphorane analogously to the production of isopropoxymethylcarbonylmethylenetriphenyl phosphorane. The title compound is obtained as crystallized oil with a melting point of 66°–70° C.

6. Cylopropylmethoxymethylcarbonylmethylenetriphenyl phosphorane

A solution of 5.58 g of sodium in 25.0 g of cyclopropylmethanol and 200 ml of toluene is reacted with 30.0 g of chloromethylcarbonylmethylenetriphenyl phosphorane analogously to the production of isopropoxymethylcarbonylmethylenetriphenyl phosphorane. The title compound is obtained as solid with a melting point of 121° C.

7. (3-Butinyl)-carbonylmethylenetriphenyl phosphorane 20.0 g of methylcarbonylmethylenetriphenyl phosphorane is dissolved in 628 ml of tetrahydrofuran and mixed by instillation at −78° C. with 41.3 ml of butyllithium (1.6 molar solution in hexane). Then,5.0 ml of propargyl bromide is instilled. The reaction mixture is added to an ice/common salt solution after heating to room temperature, and the mixture is extracted with ethyl acetate. After drying the organic phase with sodium sulfate,23.4 g of solid is obtained. Column chromatographic purification (silica gel/ ethyl acetate) yields 15.4 g of the title compound with a melting point of 135°–136° C.

8. (3-Butenyl)-carbonylmethylenetriphenyl phosphorane

By reaction of 15.0 g of methylcarbonylmethylenetriphenyl phosphorane in 471 ml of tetrahydrofuran with 31.0 ml of butyllithium and 4.28 ml of allyl bromide analogously to 7, the title compound is obtained as crystallized oil with a melting point of 92°–93° C.

By varying the keto component used for the production of the Wittig reagent, other phosphoranes, which can be reacted with aldehyde 1 or 2 analogously to other compounds of general formula IV as described below, can be obtained in a similar way.

EXAMPLE 1

A solution of 1.6 g of 1(S),3(R)-bis-(tert-butyldimethylsilyloxy)-20(R)-methyl-9,10-secopregna-5E,7E,10,(19)-triene-21-carbaldehyde in 50 ml of toluene is stirred for 16 hours at 80° C. under argon after adding 3.02 g of isoamylcarbonylmethylenetriphenyl phosphorane. Then, the solvent is removed under reduced pressure and the residue is chromatographed on silica gel with hexane/ethyl acetate. The main fraction yields 1.15 g of [1(S),3(R)-bis-(tert-butyldimethylsilyloxy)-9,10-secochola-5E,7E,10,(19),23(E)-tetraen-24-yl]-4-methyl-pentan-1-one as colorless oil.

$^1$H-NMR (CDCl$_3$): δ=0.01 ppm (s,12H,Si—CH$_3$), 0.56 (s,3H,H-18), 0.87 (s,18H,Si-t.-butyl); 0.88 (d,J=7 Hz,6H, C—(CH$_3$)$_2$), 0.95 (d,J=7 Hz,3H,H-21); 4.25 (m,1H-3); 4.55 (m,1,H-1); 4.94 and 5.00 (s; 1H, H-19 each); 5.82 and 6.46 (d,J=11 Hz; 1H, H-6, H-7 each); 6.10 (d,J=16 Hz,1H,H-24); 6.80 (m,1H,H-23).

EXAMPLE 2

572 mg of cerium(III)-chloride-heptahydrate is dissolved in 10 ml of methanol and the compound (1.10 g) produced according to example 1 dissolved in 5 ml of methanol is added. After adding 61 mg of sodium borohydride, it is stirred for 30 minutes at 0° C. For the working up, it is poured into water, extracted with dichloromethane, dried (Na$_2$SO$_4$) and concentrated by evaporation. The mixture of diastereomeric alcohols thus obtained is separated by chromatography on silica gel with hexane/ethyl acetate. In the elution sequence,290 mg of 1(S),3(R)-bis-(tert-butyldimethylsilyloxy)-24-(1-hydroxy-4-methylpentyl),-9,10-seco-5E, 7E,10(19),23(E)-cholate-traene (epimer A) and 120 mg of epimer B are obtained. The epimers show identical NMR spectra.

$^1$H-NMR (CDCl$_3$): δ=0.01 ppm (s,12H,Si—CH$_3$), 0.49 (s,3H,H-18), 0.86 (s,18H,Si-t.-butyl); 0.86 (d,J=7 Hz,6H, C—(CH$_3$)$_2$); 0.88 (d,J=7 Hz,3H,H-21); 4.16 (m, 1H,H-3); 4.48 (m, 1H,H-1); 4.88 and 4.93 (s; 1H, H-19 each); 5.40 (dd,J=15.5 and 7 Hz,1H,H-24); 5.55 (m,1H,H-23); 5.77 and 6.40 (d,J=11 Hz; 1H, H-6, H-7 each).

EXAMPLE 3

A solution of 290 mg of the product (epimer A) obtained under example 2 in 80 ml of toluene is irradiated in a pyrex immersion reactor by a high pressure mercury vapor lamp (Philips HPK 125) after adding 44 mg of anthracene and 0.01 ml of triethylamine. The irradiation time is 3.5 minutes, the thorough mixing of the solution is guaranteed by introducing a nitrogen stream. After concentration by evaporation and chromatography on silica gel with hexane/ethyl acetate,241 mg of 1(S),3(R)-bis(tert-butyldimethylsilyloxy)-24-(1-hydroxy-4-methylpentyl)-9,10-secochola-5Z, 7E,10(19),23(E)-tetraene is obtained as colorless oil.

$[α]_D^{20}$+49.6° (CHCl$_3$, c=0.425).

Analogous treatment of 120 mg of the polar isomer (epimer B) obtained according to example 2 yields 113 mg as colorless oil.

$[α]_D^{20}$+41.4° (CHCl$_3$, c+0.285)

EXAMPLE 4

A solution of 225 mg of the product obtained according to example 3 from epimer A in 5 ml of THF is stirred for 60 minutes at 60° C. after adding 1.31 ml of a 1M solution of tetrabutylammonium fluoride in THF. After cooling, it is poured into a saturated common salt solution and extracted with ethyl acetate. The crude product is chromatographed on silica gel with hexane/ethyl acetate and yields 85 mg of 24-(1-hydroxy-4-methylpentyl)- 9,10-secochola-5Z,7E, 10(19),23E-tetraene-1(S),3(R)-diol as white foam.

$^1$H-NMR (CDCl$_3$): δ=0.57 ppm (s,3H,H-18), 0.84 (d,J=7 Hz,3H,H-21); 0.92 (d,J=7 Hz,6H,C—(CH$_3$)$_2$); 4.03 (m,1H, H- 25); 4.23 (m,1H,H-3); 4.43 (m,1H,H-1); 5.00 and 5.33 (s; 1H, H-19 each); 5.45 (dd,J=15.5 and 7 Hz,1H,H-24); 5.60 (m,1H,H-23); 6.02 and 6.38 (d,J=1 Hz; 11H, H-6, H-7 each).

Analogous treatment of the product (95 mg) obtained according to example 3 from epimer B yields 35 mg of the epimeric triol as colorless oil. The NMR spectra of the epimers are identical.

EXAMPLE 5

Analogously to the process described under example 1, 2.05 g of 1(S),3(R)-bis-(tert-butyldimethylsilyloxy)-20-(R)-methyl-9,10-secopregna- 5E,7E,10(19)-triene-21-carbaldehyde in 53 ml of toluene is reacted with 3.4 g of isobutylcarbonylmethlenetriphenyl phosphorane. After chromatographic purification, [1(S),3(R)-bis-(tert-butyldimethylsilyloxy)-9,10-secochola-5E,7E,10(19),23(E)-tetraen-24-yl]-3-methyl-butan-1-one with a melting point of 79°–81° C. is obtained (from ethanol).

$[α]_D^{20}$+52.6°

EXAMPLE 6

By reduction of 1.75 g of the product obtained under example 5 under the conditions of example 2, 1(S),3(R)-bis(tert-butyldimethylsilyloxy)- 24-(l(R,S)-hydroxy-3-methylbutyl)-9,10-secochola-5E,7E,10(19),23E-tetraene is obtained as an oily mixture of the epimers. By chromatography on silica gel with hexane/ethyl acetate, 780 mg of epimer A and 600 mg of epimer B are obtained in the elution sequence as colorless oils, which cannot be differentiated by NMR spectroscopy.

EXAMPLE 7

By triplet-sensitized photoisomerization analogously to example 3 and subsequent silylether cleavage analogously to example 4, 240 mg of 24-(1-hydroxy-3-methylbutyl)-9,10-secochola-5Z,7E,10(19),23(E)-tetraene-1(S),3(R)-diol (compound A) with a decomposition interval of 119°–125° C., is obtained from 700 mg of epimer A produced according to example 6 $[\alpha]_D^{20}$+38.8° (methanol, c=0.505).

Analogous treatment of 330 mg of epimer B yields 129 mg of 24-(1-hydroxy-3-methylbutyl)-9,10-secochola-5Z, 7E,10(19),23(E)-tetraene- 1(S),3(S)-diol (compound B) with a decomposition interval of 139°–145° C., $[\alpha]_D^{20}$+ 54.8° (methanol, c=0.505).

EXAMPLE 8

A solution of 170 mg of the product obtained according to example 5 in 5 ml of THF is stirred for 90 minutes at room temperature after adding 200 mg of lithium-tri-tert-butoxy-aluminum hydride. For working up, it is mixed with 0.8 ml of saturated $NH_4Cl$ solution, filtered and the filtrate is concentrated by evaporation. Chromatography of the crude product on $Al_2O_3$ (Merck, neutral, step III) yields 108 mg of 1-[1(S),3(R)-bis-(tert-butyldimethylsilyloxy)-9,10-secochola-5E,7E,10(19)-trien-24-yl]-3-methyl-butan-1-one as colorless oil.

$^1$H-NMR ($CDCl_3$): $\delta$=0.53 ppm (s,3H,H-18); 4.22 (m,1H, H-3); 4.54 (m,1H,H-1); 4.93 and 4.98 (m; 1H, H-19 each); 5.82 and 6.46 (d,J=11 Hz; 1H, H-6, H-7 each).

EXAMPLE 9

From 100 mg of the product of example 8, photochemical double bond isomerization analogously to example 3 and silylether cleavage analogously to example 4 yield 50 mg of 1-[1(S),3(R)-dihydroxy- 9,10-secochola-5Z,7E,10(19)-trien-24-yl]-3-methyl-butan-1-one.

UV (methanol):=212 nm ($\epsilon$=14 300), 265 (15 860).

EXAMPLE 10

The reaction of 1.6 g of 1(S),3(R)-bis-(tert-butyldimethylsilyloxy)-20(R)-methyl-9,10-secopregna-5E,7E,10(19)-triene-21-carbaldehyde with (2-isopropoxyethyl)carbonyl-methylenetriphenyl phosphorane analogously to example 1 yields 1.15 g of 1-[1(S),3(R)-bis-(tert-butyldimethylsilyloxy)-9,10-secochola-5E,7E,10(19),23(E)-tetraen-24-yl]-3-isopropoxypropan-1-one as colorless oil.

$^1$H-NMR ($CDCl_3$): $\delta$=0.01 ppm (s,12H,Si—$CH_3$), 0.55 (s,3H,H-18),0.86 and 0.90 (s; 9H, Si-t.-butyl each); 0.96 (d, J=7 Hz,3H,H-21); 1.15 (d,J=7 Hz,6H,C($CH_3$)$_2$); 3.60(m,1H, CH—O); 3.73 (t,J=7 Hz,2H,$CH_2$—O); 4.23 (m,1H,H-3); 4.55 (m,1H,H-1); 4.95 and 5.00 (m; 1H, H-19 each); 5.83 and 6.46 (d,J=11 Hz; 1H, H-6, H-7 each); 6.11 (d,J=15.5 Hz,1H,H-24); 6.87 (m, 1H,H-23).

EXAMPLE 11

By reduction analogously to example 2, photoisomerization analogously to example 3 and silylether cleavage analogously to example 4, 143 mg of 24-(1(R,S)-hydroxy-3-isopropoxypropyl)-9,10-secochoa-5Z,7E,10(19),23-tetraene-1(S),3(R)-diol is obtained from 1.05 g of the product produced according to example 10 as a 1:1 mixture of the diastereomers that are separated by high-pressure liquid chromatography. The isomers exhibit identical NMR spectra.

$^1$H-NMR (CDCl3): $\delta$=0.57 ppm (s,3H,H-18),0.94 (d,J=7 Hz,3H,H-21); 1.15 (d,J=7 Hz,6H,C($CH_3$)$_2$),4.17 (m, 1H,H-3); 4.21 (m, 1H,H-25); 4.38 (m,1H,H-1); 4.98 and 5.29 (m; 1H, H-19 each); 5.45 (dd,J=15.5 and 7 Hz,1H,H-24); 5.63 (m,1H,H-23); 6.02 and 6.38 (d,J=11 Hz; 1H, H-6, H-7 each).

EXAMPLE 12

Starting fron aldehyde 1 and isopropoxymethylcarbonyl-methylenetriphenyl phosphorane, isomer B (5Z,7E,22E-1(S),3(R),24(S)-9,10-seco- 24a,24b-dihomo-24b-oxac-holesta-5,7,10(19),22 -tetraene-1,3,24-triol) with a melting point of 131°–132° C. is obtained analogously to the sequence of examples 1–4.

EXAMPLE 13

Starting fron aldehyde 1 and (2-isopropoxyethyl)-carbonylmethylenetriphenyl phosphorane, isomer B (5Z,7E,22E-1(S),3(R),24(S)-9,10-seco-24a,24b,24c-trihomo-24c-oxac-holesta-5,7,10(19),22-tetraene-1,3,24-triol) with a melting point of 125°–126° C. is obtained analogously to the sequence of examples 1–4.

EXAMPLE 14

Analogously to example 1, 0.85 g of 1(S),3(R)-bis-(tert-butyldimethylsilyloxy)- 20(R)-methyl-9,10-secopregna-5E, 7E,10(19)-triene-21-carbaldehyde is reacted with 4.5 g of cyclopropylmethylcarbonyltriphenyl phosphorane. After chromatographic purification on silica gel with hexane/ethyl acetate, 500 mg of 1(S),3(R)-bis-(tert-butyldimethylsilyloxy) 26,27-cyclo-24a,24b-dihomo-9,10-secocholesta-5E, 7E,10(19),23E-tetraen-24a-one is obtained as colorless foam.

$^1$H-NMR ($CDCl_3$): $\delta$=0.01 ppm (s,12H,Si—$CH_3$); 0.09 and 0.50 (m; 2H,H-26 and H-27 each); 0.50 (s,3H,H-18); 0.83 and 0.85 (s; 9H, Si-t.-butyl each); 0.91 (d,J=7.3 Hz,3H, H-21); 0.96 (m, 1H,H-25); 2.47 (d,J=6 Hz,2H,H-24b); 4.16 (m,1H,H-3); 4.47(m, 1H,H-1); 4.89 and 4.93(s; 1H, H-19 each); 5.77 and 6.40 (d,J=11 Hz; 1H, H-6 and H-7 each); 6.08(d,J=15.5 Hz,H-24); 6.75 (ddd,J=15.5,9,6.5 Hz,1H,H-23).

EXAMPLE 15

Reduction of the product obtained under example 14 analogously to example 2 yields 200 mg of 1(S),3(R)-bis-(tert-butyldimethylsilyloxy)- 26,27-cyclo-24a,24b-dihomo- 9,10-secocholesta- 5E,7E,10(19),23E-tetraen-24a(R,S)-ol as an oily mixture of the epimers that cannot be differentiated by NMR spectroscopy.

$^1$H-NMR ($CDCl_3$): $\delta$=0.01 ppm (s,12H,Si—$CH_3$); 0.09 and 0.40 (m; 2H, H-26 and H-27 each); 0.50 (s,3H,H-18); 0.68 (m,1H,H-25); 0.81 and 0.86 (s; 9H Si-t. -butyl each); 0.88 (d,J=7 Hz,3H,H-21); 1.40 (t,J=7 Hz,H-24b); 4.13 (m,1H,H-24a); 4.17 (m,1H,H-3); 4.49 (m,1H,H-1); 4.88 and 4.93 (s; 1H, H-19 each); 5.45 (dd,J=15.5 , 6.5 Hz,1H,H-24); 5.59 (ddd,J=15.5, 7, 6.5 Hz,1H,H-23); 5.77 and 6.40 (d,J=11 Hz; 1H, H-6 and H-7 each).

EXAMPLE 16

Analogously to example 3, by triplet-sensitized photoisomerization and cleavage of the protecting groups analogously to example 4, 86 mg of 26,27-cyclo-24a,24b-dihomo-9,10-secocholesta-5Z,7E,10(19),23E-tetraene-1(S), 3(R),24a (R,S)-triol is obtained from 190 mg of the compound described under example 15 as a 1:1 mixture of the diastereomers that are separated by high-pressure liquid chromatography. The NMR spectra of both diastereomers are identical.

$^1$H-NMR (CDCl$_3$): δ=0.09 and 0.49 (m; 2H, H-26 and H-27 each); 0.53 (s,3H,H-18); 0.70(m,1H,H-25); 0.93 (d,J=7 Hz,3H,H-21); 4.18 (m,1H,H-24a); 4.22 (m,1H,H-3); 4.43 (m,1H,H-1); 5.00 and 5.32 (s; 1H, H-19 each); 5.50 (dd,J=15.5, 6.5 Hz,H-24); 5.64 (ddd,J=15.5, 7, 6.5 Hz,1H, H-23); 6.02 and 6.38 (d,J=11 Hz; 1H, H-6 and H-7 each).

EXAMPLE 17

Starting from aldehyde 1 and (1-ethylpropoxymethyl)carbonylmethylenetriphenyl phosphorane, isomer B (5Z,7E, 22E-1(S),3(R),24(S)-26,27-dimethyl-24a,24b-dihomo-24b-oxa-9,10-secocholesta- 5,7,10(19),22-tetraene-1,3,24 -triol) with a melting point of 103–105° C. is obtained analogously to the sequence of examples 1–4.

EXAMPLE 18

Starting from aldehyde 1 and cyclopropylmethoxymethylcarbonylmethylenetriphenyl phosphorane, isomer B (5Z, 7E,22E-1(S),3(R),24(S)-26,27-cyclo-24a,24b,24c-trihomo-24b-oxa-9,10-secocholesta-5,7,10(19),22-tetraene-1, 3,24-triol) is obtained analogously to the sequence of examples 1–4.

$^1$H-NMR (DMSO-d$_6$): S=0.16 ppm (m,2H); 0.43 (m,2H); 0.53 (S,3H); 1.00 (d,J=6 Hz,3H); 3.21 (m,4H); 4.00 (m,2H); 4.19 (m, 1H); 4.51 (d,J=5 Hz,1H); 4.70 (d,J=5 Hz,1H); 4.75 (m,1H); 4.82 (d,J=5 Hz,1H); 5.21 (m,1H); 5.39 (m,2H); 5.98 (d,J=11 hz,1H); 6.18 (d,J=11 hz,1H).

EXAMPLE 19

Starting from aldehyde 1 and (3-butinyl)carbonylmethylenetriphenyl phosphorane, isomer B (5Z,7E,22E-1(S),3(R), 24(S)-24-(3-butinyl)-9,10-secochola-5,7,10 (19),22-tetraene-1,3,24-triol) with a melting point of 115°–118° C. is obtained analogously to the sequence of examples 1–4.

EXAMPLE 20

Starting from aldehyde 1 and (3-butenyl)carbonylmethylenetriphenyl phosphorane, isomer B (5Z,7E,22E-1(S), 3(R),24(S)-24-(3-butenyl)-9,10-secochola-5,7,10(19),22-tetraene-1,3,24-triol) with a melting point of 146°–147° C. is obtained analogously to the sequence of examples 1–4.

We claim:

1. Side-chain homologous vitamin D derivatives of formula I

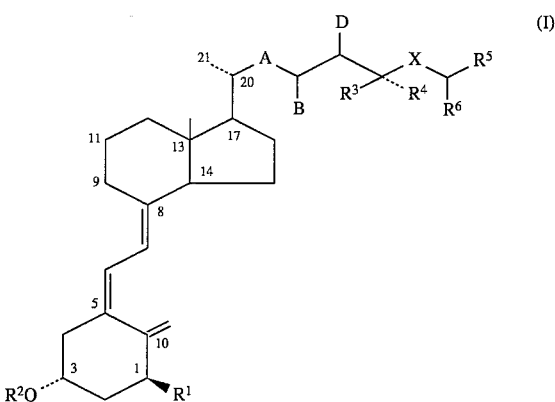

in which

R$^1$ means a hydrogen atom, a hydroxy or an acyloxy group with 1 to 9 carbon atoms, R$^2$ means a hydrogen atom or an acyl group with 1 to 9 carbon atoms, R$^3$ or R$^4$ means a hydroxy or acyloxy group with 1 to 9 carbon atoms, and the respective other substituent is a hydrogen atom or R$^3$ or R$^4$ together mean an oxygen atom, R$^5$ and R$^6$, independently of one another, each mean a linear or branched alkyl radical with up to 5 carbon atoms, a trifluoromethyl group or together a saturated, unsaturated or aromatic carbocyclic 3-, 4-, 5- or 6-member ring formed with the tertiary carbon atom or with the inclusion of 1 or 2 N, O or S atoms a heterocyclic 3, 4, 5 or 6-member ring, B and D either mean a hydrogen atom each or together a second bond (E-configured double bond) and either A means a direct bond between carbon atoms 20 and 22 and X means an oxy alkylene radical —(CH$_2$)$_n$O— with n=1 to 3 or A means a methylene bridge (—CH$_2$—) between carbon atoms 20 and 22 and X means an alkylene radical —(CH$_2$)$_n$— or an oxy alkylene radical —(CH$_2$)$_n$O— with n=1 to 3, or if A stands for a direct bond and B and D together stand for a second bond,

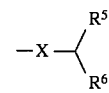

means

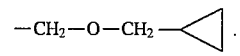.

2. Vitamin D derivatives according to claim 1, in which R$^1$ stands for a hydroxy group.

3. Vitamin D derivatives according to claim 1, in which R$^2$ stands for a hydrogen atom.

4. Vitamin D derivatives according to claim 1, in which R$^3$ or R$^4$ means a hydroxy group.

5. Vitamin D derivatives according to claim 1, in which n in X is 1 or 2.

6. Vitamin D derivatives according to claim 1, in which R$^5$ and R$^6$ stand for methyl groups.

7. Vitamin D derivatives according to claim 1, in which R$^5$, R$^6$ and the tertiary carbon atom together stand for a cyclopropyl ring.

8. 24-(1(R)-Hydroxy-4-methylpentyl),-9,10-secochola-5Z, 7E,10(19),23E-tetraene-1(S),3(R)-diol, 24-(1(S)-hydroxy-4-methylpentyl),-9,10-secochola-5Z, 7E,10(19),23E-tetraene-1(S),3(R)-diol, 24-(1(R)-hydroxy-3-methylbutyl)-9,10-secochola-5Z,7E,10(19),23E-tetraene-1(S),3(R)-diol, 24-(1(S)-hydroxy-3-methylbutyl)-9,10-secochola-5Z,7E,10(19),23E-tetraene-1(S),3(R)-diol, 24-(1(R)-hydroxy-3-methylbutyl)-9,10-secochola-5Z,7E,10(19)-triene-1(S),3(R)-diol, 24(1(S)-hydroxy-3-methylbutyl)-9,10-secochola-5Z,7E,10(19)-triene-1(S),3(R)-diol, 24-(1(R)-hydroxy-3-isopropoxypropyl)-9,10-secochola-5Z,7E,10, (19),23E-tetraene-1(S),3(R)-diol, 24-(1(S)-hydroxy-3-isopropoxypropyl)-9,10-secochola-5Z,7E,10, (19),23E-tetraene-1(S),3(R)-diol, 24-isopropoxymethyl-9,10-secochola-5Z,7E,10(19),22E-tetraene-1(S),3(R),24(R)-triol, 24-isopropoxymethyl-9,10-secochola-5Z,7E,10(19),22E-tetraene-1(S),3(R),24(S)-triol, 24-(2-isopropoxyethyl)-9,10-secochola-5Z,7E,10(19), 22E-tetraene-1(S),3(R),24(R)-triol, 24-(2-isopropoxyethyl)-9,10-secochola-5Z,7E,10(19), 22E-tetraene-1(S),3(R),24(S)-triol, 26,27-cyclo-24a,24b-dihomo-9,10-secocholesta-5Z,7E, 10(19),23E-tetraene-1(S),3(R),24a(R)-triol, or 26,27-cyclo-24a,24b-dihomo-9,10-secocholesta-5Z,7E, 10(19),23E-tetraene-1(S),3(R),24a(S)-triol.

9. A pharmaceutical preparation comprising at least one compound according to claim 1 and a pharmaceutically compatible vehicle.

10. A derivative according to claim 1, wherein A is —(CH$_2$)—.

* * * * *